(12) United States Patent
Simpson

(10) Patent No.: US 8,556,421 B2
(45) Date of Patent: Oct. 15, 2013

(54) CALCULATING AN INTRAOCULAR LENS (IOL) POWER ACCORDING TO A DIRECTLY DETERMINED IOL LOCATION

(75) Inventor: Michael J. Simpson, Arlington, TX (US)

(73) Assignee: Novartis AG, Basel (CH)

( * ) Notice: Subject to any disclaimer, the term of this patent is extended or adjusted under 35 U.S.C. 154(b) by 261 days.

(21) Appl. No.: 13/276,965

(22) Filed: Oct. 19, 2011

(65) Prior Publication Data

US 2013/0100408 A1    Apr. 25, 2013

(51) Int. Cl.
*A61B 3/10* (2006.01)
*A61F 2/16* (2006.01)

(52) U.S. Cl.
CPC ............... *A61B 3/1005* (2013.01); *A61F 2/16* (2013.01)
USPC ........................... 351/205; 351/212; 623/6.11

(58) Field of Classification Search
CPC ................................ A61B 3/1005; A61F 2/16
USPC ........................ 351/205, 212, 246; 623/6.11
See application file for complete search history.

(56) References Cited

U.S. PATENT DOCUMENTS

| | | | |
|---|---|---|---|
| 7,883,208 B2 | 2/2011 | Norrby et al. | |
| 2006/0135952 A1 | 6/2006 | Curatu et al. | |
| 2007/0260157 A1 | 11/2007 | Norrby | |
| 2008/0033408 A1 | 2/2008 | Bueler et al. | |
| 2010/0094604 A1* | 4/2010 | Gatinel et al. | 703/2 |
| 2010/0131059 A1 | 5/2010 | Callahan et al. | |
| 2011/0128502 A1 | 6/2011 | Norrby et al. | |
| 2011/0242482 A1 | 10/2011 | Olsen | |
| 2012/0069298 A1 | 3/2012 | Ng | |

FOREIGN PATENT DOCUMENTS

WO    2010/109020 A1    9/2010

OTHER PUBLICATIONS

Preufsner, P-R, et al., "Intraocular lens calculation accuracy limits in normal eyes", J. Cataract Refract Surg 2008 (May); 34:802-808.

* cited by examiner

*Primary Examiner* — Huy K Mai
(74) *Attorney, Agent, or Firm* — Keiko Ichiye

(57) ABSTRACT

In certain embodiments, calculating intraocular lens (IOL) power includes determining locations of parts of an eye along an axis of the eye. The locations include the location of a cornea, the anterior and posterior locations of a crystalline lens, and the location of a retina. An IOL location of an IOL is calculated according to the anterior and posterior locations of the crystalline lens. Corneal data is also determined. The IOL power is calculated using the corneal data, the IOL location, and the retinal location. In certain embodiments, refractive indices are determined for segments of the axis, and at least one location is adjusted according to the refractive indices.

19 Claims, 3 Drawing Sheets

CALCULATING AN INTRAOCULAR LENS (IOL) POWER ACCORDING TO A DIRECTLY DETERMINED IOL LOCATION

TECHNICAL FIELD

The present disclosure relates generally to intraocular lenses (IOLs), and more particularly to calculating an intraocular lens (IOL) power according to a directly determined IOL location.

BACKGROUND

An intraocular lens (IOL) is an artificial lens that may be implanted into an eye. The IOL refracts light by an amount described by the refractive power of the IOL. The IOL power may be calculated from features of a patient's eye. An IOL with the appropriate power should be used in order to properly correct the patient's vision. Known techniques for calculating IOL power typically make simplifying assumptions. These assumptions, however, may yield IOL power values that might not be suitable in certain situations.

BRIEF SUMMARY

In certain embodiments, calculating intraocular lens (IOL) power includes determining locations of parts of an eye along an axis of the eye. The locations include the location of a cornea, the anterior and posterior locations of a crystalline lens, and the location of a retina. An IOL location of an IOL is calculated according to the anterior and posterior locations of the crystalline lens. Corneal data is also determined. The IOL power is calculated using the corneal data, the IOL location, and the retinal location. In certain embodiments, features of the IOL, such as aspects of the optic or haptics, may be used in the calculation. In certain embodiments, refractive indices are determined for segments of the axis, and at least one location is adjusted according to the refractive indices.

BRIEF DESCRIPTION OF THE DRAWINGS

Exemplary embodiments of the present disclosure will now be described by way of example in greater detail with reference to the attached figures, in which.

DETAILED DESCRIPTION OF EXAMPLE EMBODIMENTS

Figure 1:
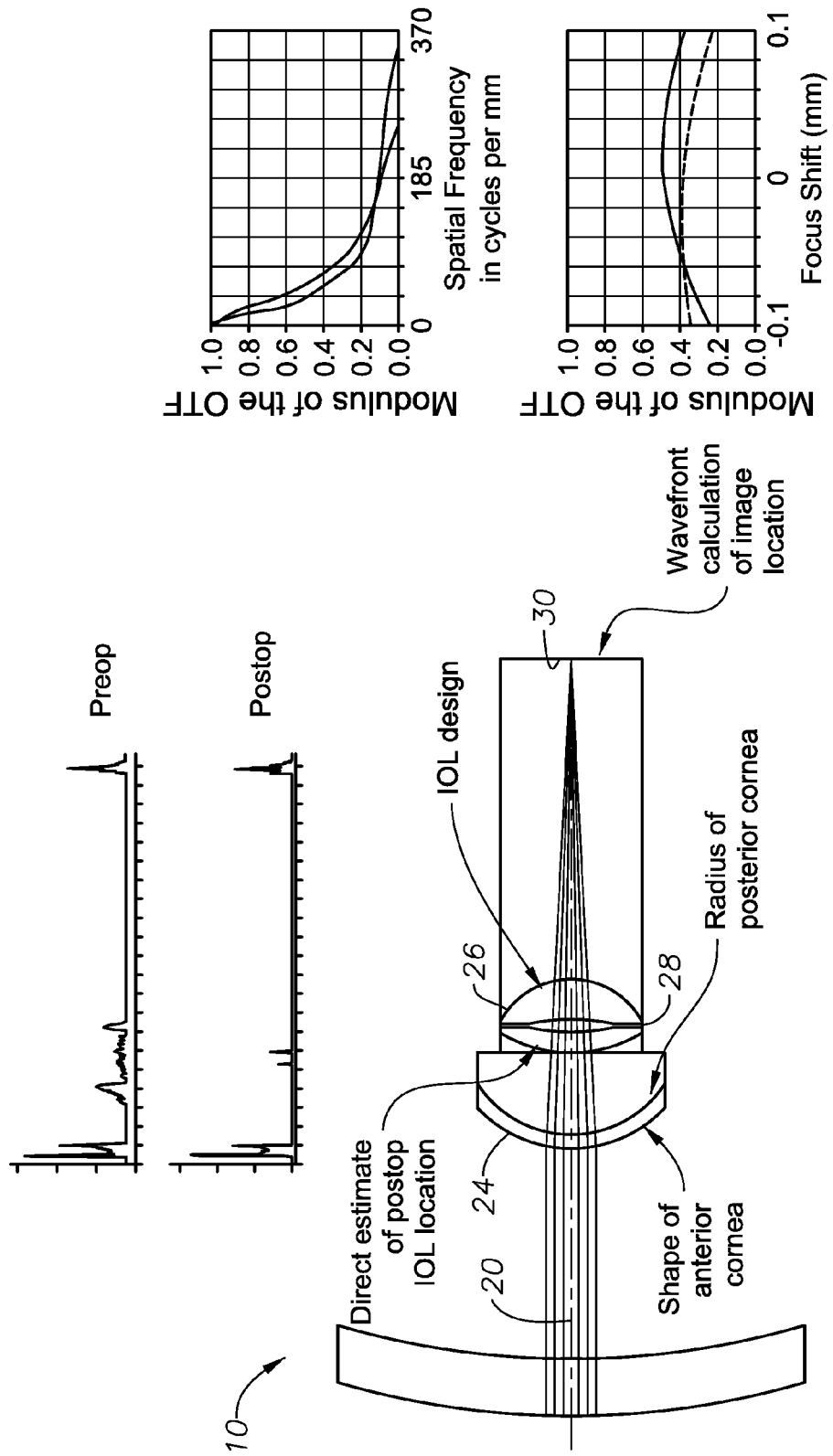
FIGS. 1 and 2 illustrate examples of a system and method for calculating intraocular lens (IOL) power.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

Figure 2:
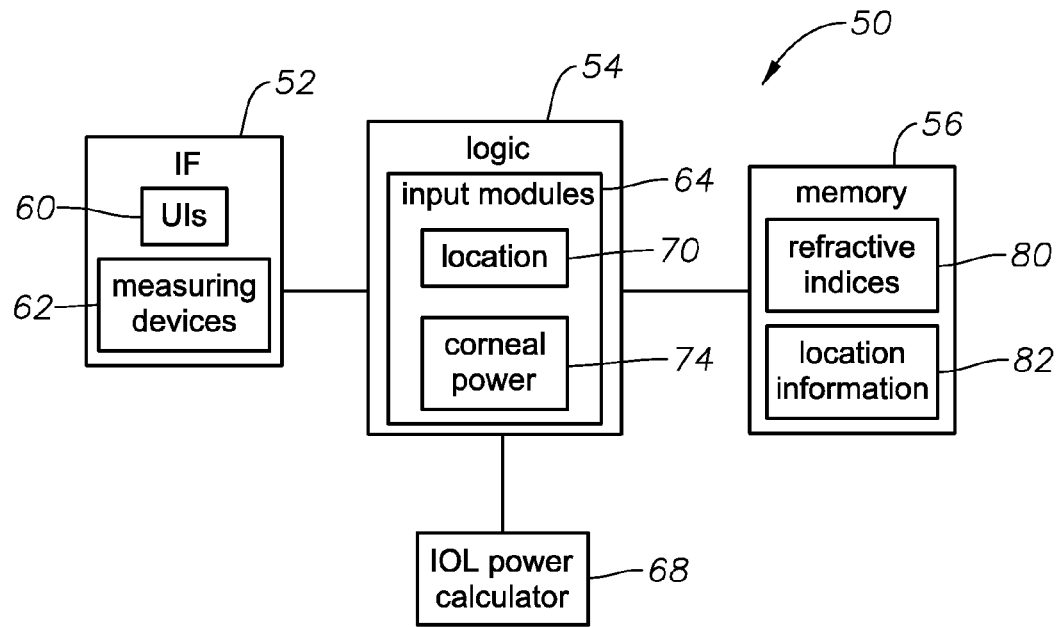

FIGS. 1 and 2 illustrate examples of a system and method for calculating intraocular lens (IOL) power. In certain embodiments, the IOL power can refer to various features of the IOL, such as a shape, size, and refractive power of the IOL. Calculating IOL power refers to determining the appropriate IOL that optimizes vision for a particular eye. The appropriate IOL may be determined using preoperative data of the eye.

FIG. 1 includes a diagram 10 that illustrates examples of parts of an eye. The parts of the eye include a cornea 24, and crystalline lens (or lens) 26, and a retina 30, as well as an axis 20 of the eye. Cornea 24 is the clear outer part of the eye that directs light to lens 26. Lens 26 is the clear part behind the iris that helps to focus light onto the retina 30. Retina 30 is the light-sensitive tissue lining at the back of the eye. Retina 30 converts light into electrical impulses that are sent to the brain through the optic nerve. Axis 20 may refer to the visual axis along which light travels through the eye to retina 30.

Diagram 10 also illustrates an intraocular lens (IOL) 28. An IOL 28 is a synthetic lens that may be implanted into an eye. IOL 28 may be a small plastic lens (or optic) with haptics that hold IOL 28 in place within the capsular bag inside of the eye. During cataract surgery, the crystalline lens material is removed from the capsular bag and postoperatively the capsular bag shrinks and holds IOL 28 in place. The capsular bag and features of IOL 28 affect the final axial location of IOL 28. Features of IOL 28 may include the IOL power and the design of IOL 28, including the shape, size (e.g., thickness and diameter), and arrangement of parts of IOL 28 such as the optic and haptics.

In certain embodiments, the calculation of IOL power may take into account certain parameters such as the power of cornea 24 and the locations of cornea 24, IOL 28, and retina 30 along axis 20. Diagram 10 illustrates examples of determining certain parameters. For example, the corneal data may take into account the shape of the cornea measured by, e.g., a topography system. The location of IOL 28 may be directly estimated, as described in more detail below. A wavefront calculation may be used to determine the IOL power from these parameters.

FIG. 2 illustrates a system 50 and may be used to calculate IOL power. System 50 includes one or more interfaces 52, logic 54, and one or more memories 56. Interfaces 52 include one or more user interfaces 60 (UIs) and one or more measuring devices 62. Logic includes one or more input modules 64 and an IOL power calculator 68. Input modules 64 include a location module 70 and a corneal data module 74. Memories 56 store information for system 50, for example, refractive indices 80 and location information 82 used by or calculated by location module 70.

System 50 may be used to create an accurate raytrace model of the eye. The model allows a user to measure postoperative physical parameters of the eye, which may be used to improve the model. System 50 may be used to accurately calculate IOL power, such as within 1 D or 0.5 D of the target power.

A UI 60 allows a user to receive output from and/or provide input to a computerized system. Examples of a UI 60 include a keyboard, display, mouse, microphone, speaker, or other user interface device. A measuring device 62 measures one or more features of an eye. Examples of measuring devices include wavefront sensors and Optical Coherence Tomography (OCT) or Optical Low Coherence Reflectometry (OLCR) optical biometers (such as a LENSTAR biometer).

Input modules 64 generate input for IOL power calculator 68 to allow calculator 68 to calculate an IOL power. Location module 70 determines the locations of certain parts of the eye along axis 20. In certain embodiments, the locations include a corneal location of a cornea, a crystalline lens anterior location of a crystalline lens, a crystalline lens posterior location of the crystalline lens, and a retinal location of a retina. The corneal location is the location of cornea 24 along axis 20. The anterior location of lens 26 is the location of the surface of lens 26 proximate to the anterior of the eye, and the posterior location of lens 26 the location of the surface of lens proximate to the posterior of the eye. The retinal location is the location of the surface of retina 30.

Location module 70 may determine a location by measuring the location or by calculating the location from one or more received measurements and/or values. For example, the axial length, crystalline lens anterior location, and/or crystalline lens posterior location may be determined by measuring with an optical biometer system.

Location module 70 may determine the location of IOL 28 by directly estimating the location from measurements. In certain embodiments, location module may calculate the IOL location according to features of the IOL and/or features of the eye (such as the corneal power, the axial length, the crystalline lens anterior location, and/or the crystalline lens posterior location). An example of this is described in more detail with reference to FIG. 3.

Location module 70 may adjust the locations to provide more accurate location values. In certain embodiments, location module 70 may determine refractive indices for segments of axis 20 and adjust a location according to the refractive indices. An example of this is described in more detail with reference to FIG. 4.

Corneal data module 74 determines data describing cornea 24, such as corneal power and topography. The corneal data may be determined in any suitable manner. In certain embodiments, the corneal data is determined according to the keratometry K value of the cornea. Keratometry is the measurement of the corneal radius of curvature, and the K value provides an estimate of the combined power of the anterior and posterior corneal surfaces. In certain embodiments, a corneal topography system may measure and generate a refractive map of the cornea. The refractive map may take into account the variation of the corneal power across the cornea.

In certain embodiments, the corneal data is determined according to the physical shape of the cornea, e.g., the anterior and posterior surfaces of the cornea. Zernike polynomials may be used to describe the topography. In some cases, the posterior corneal surface may be assumed to be spherical with a radius smaller than that of the anterior corneal surface (e.g., approximately 0.8, such as 0.84, of the anterior radius). In other cases, the surfaces of the cornea can be approximated by conic surfaces or conic toroid surfaces. Different levels of asphericity can also be utilized. In yet other cases, posterior corneal topography may be measured, e.g., by an ultrasound or Scheimpflug measurement system. In certain embodiments, the physical corneal topography can be used to create a raytrace model for the eye.

IOL power calculator 68 determines the power of IOL 28. In certain embodiments, IOL power calculator 68 calculates the IOL power from the corneal data, the IOL location, and the retinal location. The IOL power may be determined such that IOL 28 (in combination with cornea 24) focuses an image at the location of retina 30. For example, an IOL of approximately correct power is inserted into an eye model, and the IOL power is then adjusted until the image is in focus. The focus location may be calculated according to any suitable method, e.g., using specific rays, calculated wavefront, through-focus modulation transfer function (MTF), or other aspect of focused light. In certain embodiments, IOL power calculator 68 may include raytrace or other suitable software. In certain embodiments, the haptics may be considered when determining the optic location.

In certain embodiments, the calculation of the IOL power may take into account other factors. For example, the pupil diameter may be measured and used in the calculation. As another example, the decentration of the pupil with respect to the cornea may be taken into account.

Figure 3:
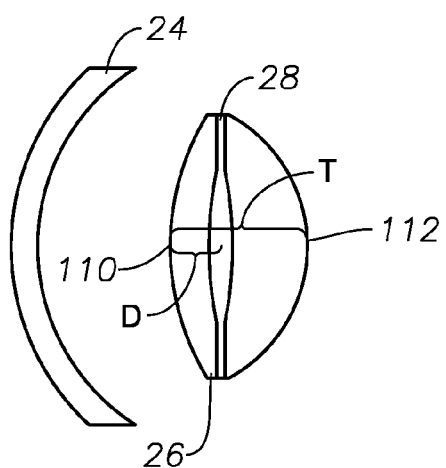
FIG. 3 illustrates an example of a method for calculating the location of an IOL.

FIG. 3 illustrates an example of a method for calculating the location of an IOL. In certain embodiments, the IOL location may be calculated as a predetermined proportional distance between a crystalline lens anterior location 110 and a crystalline lens posterior location 112.

In the example, thickness T is the distance between anterior location 110 and posterior location 112. The thickness of the IOL optic (and other features of the IOL) may vary with IOL power. An IOL of the approximate required power may be used when calculating the IOL location. The IOL location may be described by distance D, where IOL 28 is distance D behind anterior location 110. Any suitable part of the IOL may be used as the reference point of the IOL, such as the center of the haptic, the anterior IOL surface, the anterior or center of the optic edge, or the center of the optic. The IOL location may be estimated in any suitable manner. In certain embodiments, distance D may be a predetermined proportion of thickness T. For example, distance D may be a value in the range of 0.3 to 0.7×thickness T, such as D=0.4 T.

In certain embodiments, distance D may be determined from clinical data by comparing postoperative locations with preoperative parameters and determining correlations between the locations and parameters.

Figure 4:
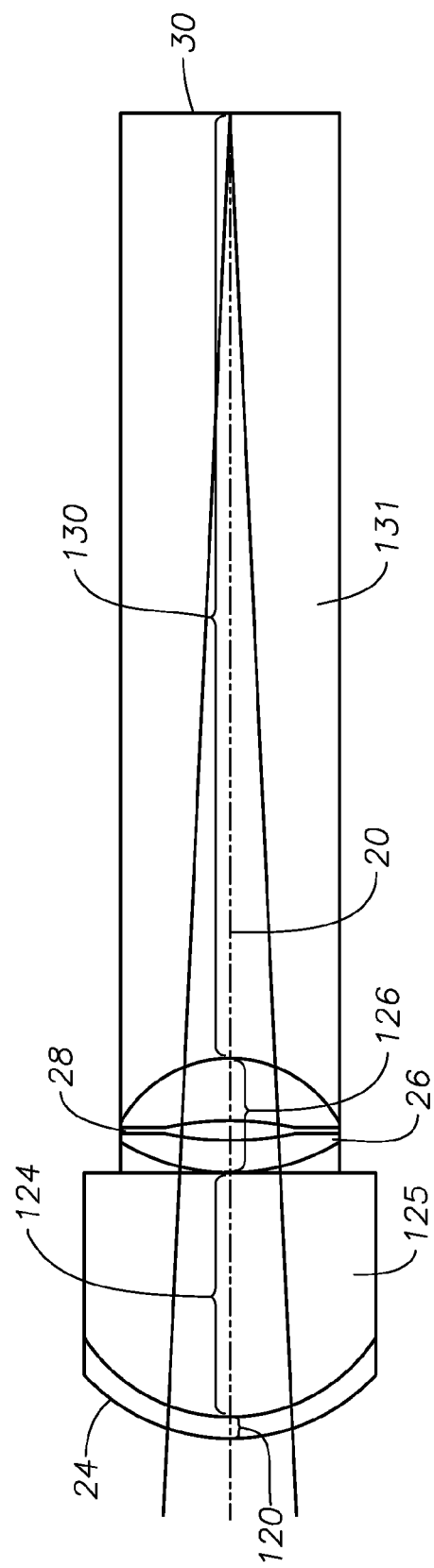
FIG. 4 illustrates an example of a method for adjusting lengths using refractive indices.

FIG. 4 illustrates an example of a method for adjusting distances using refractive indices. In the illustrated example, axis 20 may be divided into different segments that each pass through different media corresponding to different portions of the eye. A corneal segment 120 passes through cornea 24, an aqueous humor segment 124 through aqueous humor 125, a crystalline lens segment 126 through lens 26, and a vitreous humor segment 130 through vitreous humor 131.

The optical distance (or length) of a path of light through a medium is the product of the physical distance (or length) of the light path and the index of refraction of the medium. The refractive index may be, e.g., a group refractive index. Measuring devices typically measure distances along axis 20 as optical distances. An optical distance may be converted to a physical distance using a refractive index. Known measuring devices typically use the same refractive index (such as an average refractive index) for all the different segments along axis 20. Certain embodiments, however, use different refractive indices for different media along axis 20, which may improve accuracy.

In these embodiments, an optical length of each segment may be determined. Any suitable segments described herein may be used, e.g., segments between the anterior corneal location and the retinal location. A refractive index of each segment may be determined. A physical length of each segment may be calculated according to the optical length and the refractive index of the segment. One or more locations may be adjusted in accordance with the calculated physical length. For example, the locations may be adjusted to match the physical length.

The optical lengths of the segments may be determined in any suitable manner. In certain embodiments, estimated physical lengths for the segments may be obtained. One or more estimated refractive indices that were used to determine the physical lengths may also be obtained. The optical length may be calculated for each segment according to the estimated physical length of the segment and the estimated refractive indices.

The refractive indices may be determined in any suitable manner. In some cases, the refractive indices may be accessed from a memory. For example, the actual refractive index of the IOL may be stored in and accessed from a memory. In other cases, the refractive indices may be calculated from empirical data. For example, length pairs that estimate a physical length of at least a portion of the axis before and after an IOL operation may be obtained. Each pair may comprise a pre-operative physical length and a post-operative physical length. The post-operative physical length may comprise an IOL thickness of an IOL inserted during the operation. In certain cases, e.g., when an average refractive index is used to scale data from preoperative and postoperative eyes, the axial lengths may appear to be different. Refractive indices that, for each pair, yield the pre-operative physical length substantially equal to the post-operative physical length may be determined. For example, the refractive indices may be adjusted until the axial lengths are the same. The refractive indices that yield the same lengths may be regarded as the more accurate values.

Any suitable values may be used in the calculation. For example, the IOL thickness may be determined by directly measuring the physical IOL thickness or by measuring the IOL in the eye. In certain cases, one or more values may be adjusted so that they describe the physical situation more or less accurately. For example, a raytrace model may be a model that is more accurate or one that is better for IOL prediction.

In certain embodiments, an IOL location may be calculated using the physical lengths. In these embodiments, a length of a crystalline lens segment may be determined. From the length of the crystalline lens segment and the lengths of the other segments, a crystalline lens anterior location and a crystalline lens posterior location may be determined. The IOL location may then be calculated from the crystalline lens anterior location, the crystalline lens posterior location, and other parameters. For example, the IOL location may be calculated using:

$$ACD_{IOL}=C_0+C_1*ACD_{preop}+C_2*LT_{preop}+C_3*AL+C_4*K_{mean}$$

where $ACD_{IOL}$ represents the predicted anterior chamber depth (ACD) of the IOL, $C_0$ is a constant offset, $ACD_{preop}$ represents the pre-operative ACD of the crystalline lens, $LT_{preop}$ represents the pre-operative crystalline lens thickness, AL represents the axial length of the eye, and $K_{mean}$ represents the average corneal power. ACD may denote the distance from the anterior surface of the cornea to the anterior surface of the IOL. A set of eyes can be measured preoperatively and postoperatively to determine the coefficient values. Any suitable values may be used for the coefficients, such as, $C_0=[-8, -1]$, e.g., $C_0=-3.774$; $C_1=[0.5, 0.9]$, e.g., $C_1=0.675$; $C_2=[0.1, 0.7]$, e.g., $C_2=0.356$; $C_3=[0, 0.3]$, e.g., $C_3=0.091$; and $C_4=[0, 0.3]$, e.g., $C_4=0.056$.

In other embodiments, the distance to a physical reference location for the IOL, such as the center of the haptics, may be used. The reference location may be determined using:

$$ACD_{IOL}+D=C_0+C_1*ACD_{preop}C_2*LT_{preop}C_3*AL+C_4*K_{mean}$$

where D is the distance from the anterior surface of the IOL to the reference plane. Distance D may be different for different IOL powers. The actual optical and physical design of the IOL with the correct approximate power may be used for IOL power calculation.

In certain embodiments, an IOL power may be calculated using the physical lengths. The IOL location and corneal data may be determined as described herein. The retinal location may be determined from the physical lengths. The IOL power of the IOL may then be calculated according to the corneal data, the IOL location, and the retinal location.

A component of the systems and apparatuses disclosed herein may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A method for calculating intraocular lens (IOL) power comprising:
   determining a plurality of locations of parts of an eye along an axis of the eye, the locations comprising a corneal location of a cornea, a crystalline lens anterior location of a crystalline lens, a crystalline lens posterior location of the crystalline lens, and a retinal location of a retina;
   calculating an IOL location of an IOL according to the crystalline lens anterior location and the crystalline lens posterior location;
   determining corneal data of the cornea; and
   calculating the IOL power of the IOL according to the corneal data, the IOL location, and the retinal location.

2. The method of claim 1, the calculating the IOL location further comprising:
   calculating the IOL location according to a predetermined proportional distance between the crystalline lens anterior location and the crystalline lens posterior location.

3. The method of claim 1, the calculating the IOL location further comprising:
   calculating the IOL location according to one or more features of the IOL.

4. The method of claim 1, the calculating the IOL location further comprising:
   calculating the IOL location according to one or more features of the eye.

5. The method of claim 1, the determining the locations further comprising:
   determining a refractive index of each segment for a plurality of segments of the axis to yield a plurality of refractive indices; and
   adjusting at least one location according to the refractive indices.

6. The method of claim 1, the determining the corneal data further comprising determining the corneal data according to a corneal topography of the cornea.

7. The method of claim 1, the determining the corneal data further comprising determining the corneal data according to a K value of the cornea.

8. The method of claim 1, the calculating the IOL power further comprising:
   determining the IOL power that places a focal point at the retinal location.

9. A system for calculating intraocular lens (IOL) power comprising:
   a memory configured to store location information; and
   one or more processors configured to:
      determine a plurality of locations of parts of an eye along an axis of the eye, the locations comprising a corneal location of a cornea, a crystalline lens anterior location of a crystalline lens, a crystalline lens posterior location of the crystalline lens, and a retinal location of a retina;
      calculate an IOL location of an IOL according to the crystalline lens anterior location and the crystalline lens posterior location;
      determine corneal data of the cornea; and
      calculate the IOL power of the IOL according to the corneal data, the IOL location, and the retinal location.

10. The system of claim 9, the calculating the IOL location further comprising:
    calculating the IOL location according to a predetermined proportional distance between the crystalline lens anterior location and the crystalline lens posterior location.

11. The system of claim 9, the calculating the IOL location further comprising:
    calculating the IOL location according to one or more features of the IOL.

12. The system of claim 9, the calculating the IOL location further comprising:
    calculating the IOL location according to one or more features of the eye.

13. The system of claim 9, the determining the locations further comprising:
    determining a refractive index of each segment for a plurality of segments of the axis to yield a plurality of refractive indices; and
    adjusting at least one location according to the refractive indices.

14. The system of claim 9, the determining the corneal data further comprising determining the corneal data according to a corneal topography of the cornea.

15. The system of claim 9, the determining the corneal data further comprising determining the corneal data according to a K value of the cornea.

16. The system of claim 9, the calculating the IOL power further comprising:
    determining the IOL power that places a focal point at the retinal location.

17. One or more non-transitory computer-readable media storing logic for calculating intraocular lens (IOL) power, when executed by one or more processors the logic configured to:
    determine a plurality of locations of parts of an eye along an axis of the eye, the locations comprising a corneal location of a cornea, a crystalline lens anterior location of a crystalline lens, a crystalline lens posterior location of the crystalline lens, and a retinal location of a retina;
    calculate an IOL location of an IOL according to the crystalline lens anterior location and the crystalline lens posterior location;
    determine corneal data of the cornea; and
    calculate the IOL power of the IOL according to the corneal data, the IOL location, and the retinal location.

18. The non-transitory computer-readable media of claim 17, the calculating the IOL location further comprising:
    calculating the IOL location according to a predetermined proportional distance between the crystalline lens anterior location and the crystalline lens posterior location.

19. The non-transitory computer-readable media of claim 17, the determining the locations further comprising:
    determining a refractive index of each segment for a plurality of segments of the axis to yield a plurality of refractive indices; and
    adjusting at least one location according to the refractive indices.

* * * * *